US009110046B2

(12) United States Patent
Gisler et al.

(10) Patent No.: US 9,110,046 B2
(45) Date of Patent: Aug. 18, 2015

(54) MOBILE TIP WASTE RACK AND METHODS THEREOF

(71) Applicant: Roche Molecular Systems, Inc., Pleasanton, CA (US)

(72) Inventors: Andreas Gisler, Thalwil (CH); Robert Huesler, Root (CH); Manu Kottuppallil Mathew, Rotkreuz (CH); Thomi Merk, Sempach Station (CH)

(73) Assignee: ROCHE MOLECULAR SYSTEMS, INC., Pleasanton, CA (US)

( * ) Notice: Subject to any disclaimer, the term of this patent is extended or adjusted under 35 U.S.C. 154(b) by 136 days.

(21) Appl. No.: 14/012,045

(22) Filed: Aug. 28, 2013

(65) Prior Publication Data

US 2014/0064902 A1    Mar. 6, 2014

(30) Foreign Application Priority Data

Aug. 31, 2012   (EP) ..................................... 12182510

(51) Int. Cl.
*G01N 35/10*   (2006.01)
*G01N 35/02*   (2006.01)
*G01N 35/00*   (2006.01)

(52) U.S. Cl.
CPC .......... *G01N 35/1081* (2013.01); *G01N 35/026* (2013.01); *G01N 35/10* (2013.01); *G01N 2035/00277* (2013.01); *G01N 2035/103* (2013.01)

(58) Field of Classification Search
None
See application file for complete search history.

(56) References Cited

U.S. PATENT DOCUMENTS

| 4,478,094 | A | * | 10/1984 | Salomaa et al. ........... 73/863.32 |
| 5,125,748 | A | * | 6/1992 | Bjornson et al. ............... 356/414 |
| 5,213,764 | A | * | 5/1993 | Kerr et al. ...................... 422/511 |
| 5,578,270 | A | | 11/1996 | Reichler et al. |
| 6,506,610 | B1 | | 1/2003 | Fassbind et al. |
| 7,360,984 | B1 | | 4/2008 | Sugiyama et al. |
| 7,541,001 | B2 | * | 6/2009 | Kraemer et al. ................. 422/65 |
| 2001/0005489 | A1 | * | 6/2001 | Roach et al. .................... 422/99 |
| 2002/0104389 | A1 | * | 8/2002 | Hovey ......................... 73/864.17 |
| 2003/0031542 | A1 | * | 2/2003 | Hamel et al. ............. 414/331.05 |
| 2004/0005245 | A1 | * | 1/2004 | Watson et al. .................. 422/65 |
| 2004/0191120 | A1 | | 9/2004 | Yanagawa |
| 2005/0042138 | A1 | | 2/2005 | Ueda et al. |

(Continued)

FOREIGN PATENT DOCUMENTS

| JP | 6109745 | A3 | 4/1994 |
| JP | 11083868 | A2 | 3/1999 |

(Continued)

*Primary Examiner* — Jill Warden
*Assistant Examiner* — Benjamin Whatley
(74) *Attorney, Agent, or Firm* — M. Reza Savari

(57) ABSTRACT

A method of wasting tips in an automated processing module is disclosed, which includes at least three positions for holding sample racks. One of the positions is a tip waste rack position holding a tip waste rack, which includes tip receiving openings. Furthermore, it includes a SWAP rack holding mechanism for temporarily holding a sample rack. The method includes transferring the tip waste rack from the tip waste rack position to an adjacent sample rack position. Once the tip waste rack is placed in the adjacent sample rack position, the error pipette tip is discarded into one of the tip receiving openings of the tip waste rack. Following this, the tip waste rack is transferred back to the tip waste rack position. The sample rack temporarily placed in the SWAP rack holding mechanism is transferred from the SWAP rack holding mechanism to the adjacent sample rack position.

12 Claims, 3 Drawing Sheets

(56) References Cited

U.S. PATENT DOCUMENTS

| | | | |
|---|---|---|---|
| 2005/0265900 A1* | 12/2005 | Gard et al. | 422/100 |
| 2006/0269447 A1 | 11/2006 | Ruddock | |
| 2007/0020748 A1 | 1/2007 | Motegi et al. | |
| 2007/0180935 A1* | 8/2007 | Angus et al. | 73/864.14 |
| 2010/0126286 A1* | 5/2010 | Self et al. | 73/863.81 |
| 2010/0136563 A1 | 6/2010 | Keller et al. | |
| 2011/0177489 A1 | 7/2011 | Takahashi et al. | |

FOREIGN PATENT DOCUMENTS

| | | |
|---|---|---|
| JP | 2000193670 A2 | 7/2000 |
| JP | 2001296304 A3 | 10/2001 |
| WO | 9722882 A1 | 6/1997 |

\* cited by examiner

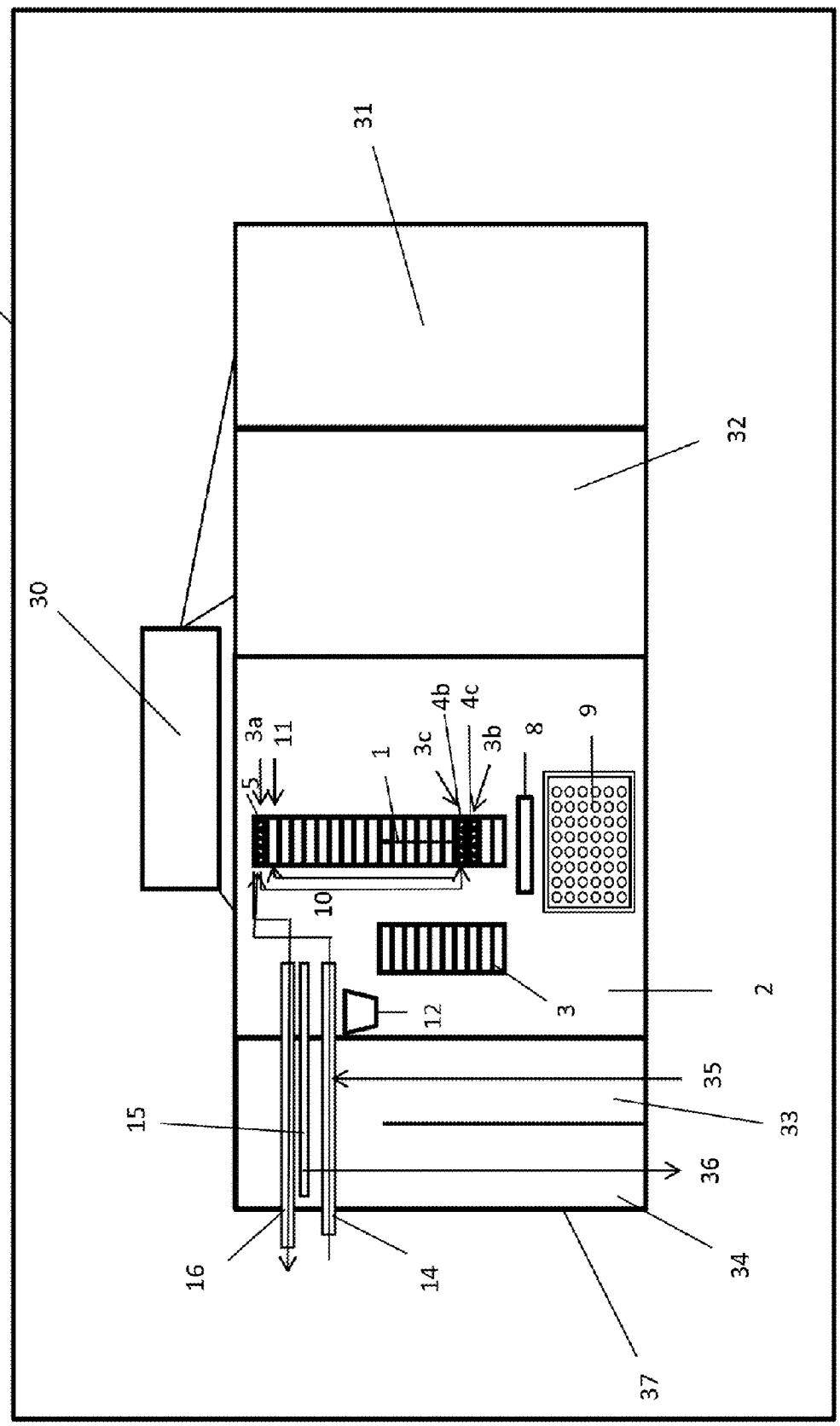

MOBILE TIP WASTE RACK AND METHODS THEREOF

CROSS-REFERENCES TO RELATED APPLICATIONS

The present application claims the benefit of priority under 35 U.S.C. §119 of EP12182510.3, filed Aug. 31, 2012, the content of which is incorporated by reference herein in its entirety.

FIELD OF THE INVENTION

The present invention relates to the field of diagnostic analyzers and automated methods performed in diagnostic analyzers.

BACKGROUND OF THE INVENTION

The present invention relates to the field of diagnostic analyzers and automated methods performed in diagnostic analyzers. Those methods commonly involve transfer of liquid samples. During such transfer processes, errors may occur. If an error occurs, the pipette tip for which an error is detected has to be removed from the system. Embodiments of the present invention, thus, relates to a method of wasting tips in an automated processing module, a processing system and an automated process for transferring samples.

Different methods for wasting pipette tips are known. One method includes discarding an error tip into the respective sample (JP2000193670). In cases where the error was not caused by the sample itself, this has the disadvantage that the sample has to be discarded and cannot be reused. Another known method involves providing a holder integrated in a processing tube for holding the tip used for transferring a specific sample, and to, in case of an error, replacing the tip in this holder and aborting further analysis of the sample (U.S. Pat. No. 6,506,610). A further method relies on the use of a fixed tip waste park in which error tips may be placed (JP2001296304). These fixed tip waste parks have two disadvantages: on the one hand, it may be necessary to transport an error tip over rows of sample tubes comprising different samples, causing an increased risk of contaminating these samples due to aerosols or droplets released from the error tip. The other disadvantage is that once the fixed tip waste rack is filled with error tips, it has to be removed manually, resulting in another risk of contamination.

The present disclosure provides a new method, system and process for wasting tips and transferring samples.

SUMMARY OF THE INVENTION

An embodiment of the present invention relates to an automated method of wasting tips in an automated processing module. The processing module comprises at least three positions for holding sample racks. One of said positions is a tip waste rack position holding a tip waste rack, wherein said tip waste rack comprises tip receiving openings. At least two of the positions are sample rack positions for holding sample racks. At least one of the sample rack positions comprises a sample rack comprising sample tubes holding a liquid sample. Two of the sample rack positions are adjacent of each other. The processing module further comprises a pipette head for transferring the samples from the sample tubes to processing tubes using pipette tips, and at least one rack transport mechanism. Furthermore, it comprises a SWAP rack holding mechanism for temporarily holding a sample rack.

The method comprises detecting an error in at least one pipette tip used for transferring the samples from the sample tubes held in a sample rack to the processing tubes. Following error detection, a sample rack, if present, is transferred from the adjacent sample rack position to an empty SWAP rack holding position within the processing module. The tip waste rack is transferred from the tip waste rack position to the adjacent sample rack position. Once the tip waste rack is placed in the adjacent sample rack position, the at least one pipette tip for which an error was detected is discarded by ejecting it from the pipette head into one of the tip receiving openings of the tip waste rack. Following this process, the tip waste rack is transferred to the tip waste rack position. The sample rack placed in the SWAP rack holding mechanism is transferred from the SWAP rack holding mechanism to the adjacent sample rack position.

A processing system comprising a processing module comprising at least three positions for holding sample racks, at least one sample rack comprising tubes holding a liquid sample located in one of said at least three positions; at least one tip waste rack comprising tip receiving openings located in another of said at least three positions; a SWAP rack holding mechanism; at least one processing tube, a pipette head for transferring samples from a sample tube to a processing tube.

An automated process of transferring samples from a sample tube to a processing tube in a processing module, comprising checking the loading status of tip receiving openings in a tip waste rack present in said processing module, wherein said loading status is either empty or loaded with a pipette tip, wherein said transferring of sample proceeds if a minimum of empty tip receiving openings is present in said tip waste rack.

BRIEF DESCRIPTION OF THE FIGURES

Other and further objects, features and advantages of the embodiments will appear more fully from the following description. The accompanying drawings, together with the general description given above and the detailed description given below, serve to explain the principles of the embodiments.

FIG. 4 shows a schematic view of a processing system with computer controller and processing module.

DETAILED DESCRIPTION OF THE INVENTION

Figure 1:
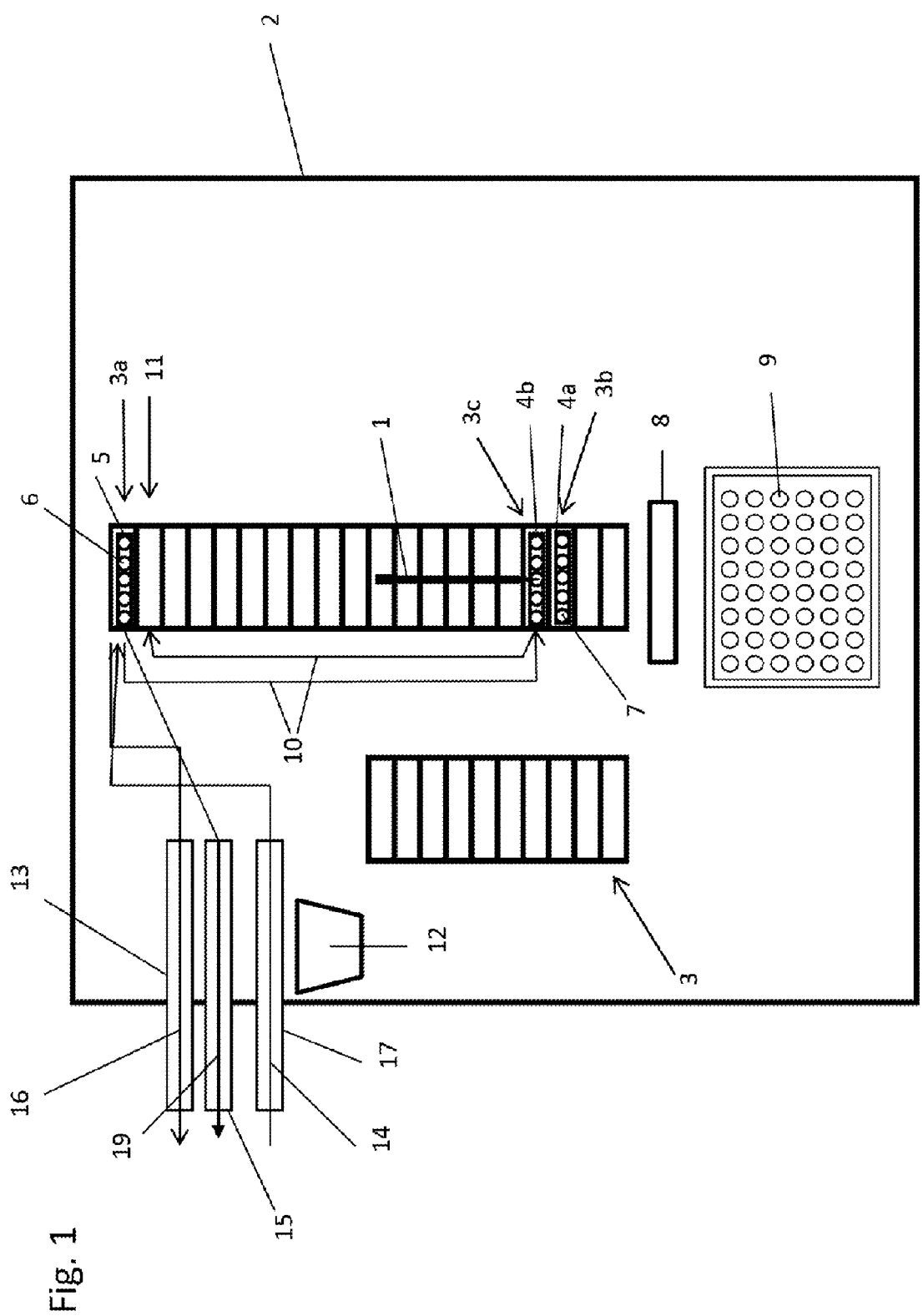
FIG. 1 shows a schematic view of a processing module with positions for holding sample racks and the tip waste rack.

By way of illustration, specific exemplary embodiments in which the invention may be practiced now are described.

One embodiment relates to an automated method of wasting tips in an automated processing module. The processing module comprises at least three positions for holding sample racks. One of said positions is a tip waste rack position holding a tip waste rack, wherein said tip waste rack comprises tip receiving openings. At least two of the positions are sample rack positions for holding sample racks. At least one of the sample rack positions comprises a sample rack comprising sample tubes holding a liquid sample. Two of the sample rack positions are adjacent of each other. The processing module further comprises a pipette head for transferring the samples from the sample tubes to processing tubes using pipette tips and at least one rack transport mechanism. Furthermore, it comprises a SWAP rack holding mechanism for temporarily holding a sample rack.

The method comprises detecting an error in at least one pipette tip used for transferring the samples from the sample tubes held in a sample rack to the processing tubes. Following error detection, a sample rack, if present, is transferred from the adjacent sample rack position to an empty SWAP rack holding position within the processing module. The tip waste rack is transferred from the tip waste rack position to the adjacent sample rack position. Once the tip waste rack is placed in the adjacent sample rack position, the at least one pipette tip for which an error was detected is discarded by ejecting it from the pipette head into one of the tip receiving openings of the tip waste rack. Following this process, the tip waste rack is transferred to the tip waste rack position. The sample rack placed in the SWAP rack holding mechanism is transferred from the SWAP rack holding mechanism to the adjacent sample rack position.

The method described herein has the advantage that error tips can be removed from the processing system with a minimized risk of contaminating other samples present in the processing system because a tip for which an error was detected and which may potentially generate aerosols of from which liquid may drop is not moved over other samples to remove the error tip, but is moved only a short distance to the tip waste rack in the adjacent sample rack position holding the tip waste rack. A further advantage is that the waste generated with the present method is minimized. Furthermore, as the method is automated, it reduces the number of user interactions, which provides extended walk away time and less user hands-on time. There is also no need to interrupt the process to remove error tips.

The term "wasting tips" relates to the removal of tips which are no longer of use from a system or device or module. In one embodiment, wasting tips means that error tips are removed from the system or device or module.

The term "processing module" relates to an independent unit or a unit which is a part of a larger apparatus, in which samples are processed. Processing includes transfer of samples from one tube to another.

The term "positions for holding sample racks" relates to positions in the processing modules which can hold a sample rack. When a sample rack is held in a position for holding a sample rack, the sample rack can be accessed by tips engaged to interfaces on a pipette head. A position for holding sample racks is, thus, a position within the processing module which presents the contents of a sample rack to a pipette head.

In one embodiment, a position for holding a sample rack which, at any one point of the workflow, holds a sample rack, even only temporarily, is a sample rack position. A tip waste rack position is a position which holds a tip waste rack during those parts of the sample transfer workflow in the processing device during which no wasting of tips is required. Thus, the tip waste rack position is a storage position for the tip waste rack. If wasting of at least one tip is required, the tip waste rack is temporarily removed from the tip waste rack position until the tip has been wasted, and is then transferred back to the tip waste rack position. The tip waste rack position always holds a tip waste rack when the method is initiated. Thus, the term "the processing module comprises a tip waste rack position holding a tip waste rack" is understood to mean that a tip waste rack is present in said tip waste rack position unless it is transferred to the adjacent position during tip waste removal. The term does, thus, include a temporary absence of the tip waste rack from the tip waste rack position in the processing module. The processing module always comprises a tip waste rack position that holds a tip waste rack at the start of the method.

An adjacent sample rack position is a sample rack position which is located directly adjacent to a sample rack position from which a liquid sample is to be transferred when a tip error is detected. Thus, the sample rack position from which liquid sample is to be transferred when a tip error is detected and the adjacent rack position are adjacent to each other. The adjacent sample rack position may hold a sample rack when the tip error is detected, or it may not hold a sample rack when the tip error is detected, and will be temporarily used to hold a tip waste rack in proximity of the sample rack position from which liquid sample is to be transferred when a tip error is detected.

Sample racks are racks which hold samples which are transferred to processing tubes in a processing module. In one embodiment, the sample rack holds at least one tube which comprises a liquid sample.

A tip waste rack is a rack which receives error tips. It relates to a rack which has dimensions that allow the tip waste rack to be held in a position for holding sample racks. In one specific embodiment, the tip waste rack has essentially the same dimensions as a sample rack used in the same processing module. In one specific embodiment, the tip waste rack has the same dimensions as a sample rack. This means that the length, width and height of tip waste rack and sample rack are the same.

Tip receiving openings are openings in the tip waste rack that can receive pipette tips. In one specific embodiment, the tip receiving openings are integrally formed openings. In another specific embodiment, the tip waste rack is a sample rack which comprises tip waste tubes. One specific embodiment of tip waste tubes are sample tubes in which a sample or a liquid sample is absent.

Thus, sample racks and tubes used in the processing module can be used for the tip wasting mechanism without any need for further consumables and hardware.

Sample tubes are tubes which comprise a sample. The sample is introduced into the processing module by loading a sample rack comprising a sample tube with the sample into the processing module. Sample tubes fit into sample racks. A "sample tube" is either a sample collection test tube, also called "primary tube", which is used to receive a sample from a patient and to transport the sample contained therein to an analytical laboratory for diagnostics purposes, or a "secondary tube", which may be used to receive an aliquot of a sample from a primary tube. A primary sample tube is typically made of glass or plastics, can assume different shapes and colors, typically associated with the type of tube, i.e. the type of sample therein or the type of conditions the sample therein is subjected to. A secondary tube is typically made of plastics and may, in one embodiment, have a lower degree of variation of size and type with respect to primary tubes. In particular, secondary tubes may be smaller than primary tubes.

The term "processing tubes" relates to tubes in which the samples or aliquots thereof are treated following transfer from the sample tubes. Treatment may include enrichment, purification, or a reaction with reagents to obtain a measurable signal. In one embodiment, processing tubes may be individual tubes made of glass or plastic. In another embodiment, processing tubes may be vessels integrally formed in a rack. In a more specific embodiment, the processing tubes are vessels of a multiwell plate.

A sample is a material which is subjected to a diagnostic test to measure one or more analytes. A sample may be a solid material which is liquidified, or may be a body fluid, such as blood, serum, plasma, urine, milk, saliva, cerebrospinal fluid, etc. A liquid sample, is a sample which is either liquid, or is liquified. Sample aliquots are portions of a sample which are employed for testing. Sample aliquots are typically generated by pipetting a portion of a sample into a secondary tube or a well where then further treatment is conducted. When two or more aliquots of a sample are needed it is for example possible to aspirate a volume of that sample and to discharge portions of that volume into two or more wells.

The term "pipette head" relates to a fluid transfer device. In one specific embodiment, a pipette head comprises at least two interfaces for engaging with pipette tips. In another specific embodiment, the number of interfaces for engaging with pipette tips is equal to the number of tip receiving openings of the tip waste rack. When engaged to the pipette tips, the pipette head can, thus, transfer samples from a sample tube to a processing tube. In one specific embodiment, the number of tip receiving openings and interfaces for engaging pipette tips are identical.

Pipette tips are disposable tips which are normally made of plastic and are reversibly engaged with a pipette head for transferring liquid samples.

A rack transport mechanism is a mechanism which can transport racks. The rack transport mechanism may comprise a conveyor. The rack transport mechanism may also comprise a gripper attached to a robotic arm.

SWAP rack holding mechanism may, in one embodiment, be a second rack transport mechanism which can temporarily hold a sample rack from an adjacent sample rack position, or it may be a dedicated SWAP rack holding position to which the adjacent sample rack is transferred temporarily. The second embodiment has the advantage that only one rack transport mechanism is required to transport sample racks in the process cell.

An empty SWAP rack holding position is a position for temporarily holding an adjacent sample rack and which remains empty while no tip wasting is required in the process cell.

Detecting an error in a pipette tip renders a tip into an error tip. Error detection relates to a mechanism to detect an error in a tip. In one specific embodiment, the error detection comprises clot detection and liquid level detection failure. Error detection may further comprise handling failure, mechanical errors, software failure or hardware failure. In the case of software or hardware failure leading to a stop of the analytical process, it may be possible that tips are still connected to the interface of the pipette head and need to be removed before restarting. This removal may also be carried out by the present method.

Once an error is detected for a specific tip, the tip is placed into a tip receiving opening of the tip waste rack and is discarded by ejecting. In one specific embodiment, the tip is discarded by selective tip detachment from the pipette head. Mechanisms for ejecting tips from pipette heads are well known in the art.

One advantage of the method is that no fixed tip waste station is needed. Such a fixed tip waste station would require additional footprint. Thus, according to the present method, tips can be wasted without need of additional footprint or additional stations. In the embodiment where the tip waste rack is a sample rack which comprises sample tubes without sample, no additional hardware, including consumables and racks, are needed to waste tips. Another advantage is that after a tip has been identified as erroneous when pipetting a specific sample and has been wasted according to the present method, it is possible to further process the respective sample, e.g. if the error is caused by the pipette tip and not by the sample. Thus, sample loss can be minimized.

A further advantage of the present method is that there is reduced contamination risk and increased safety because an error tip is directly removed from the process at the position where it is used in the process. Cross-contamination is also reduced because the error tip is not transported along a long distance, and is not moved over other samples. Furthermore, the method provides for less user hands-on time and higher increased walk-away time.

The method is advantageous as it has no negative impact on downstream processing of other samples, and does not affect workflow or throughput. In addition, the wasting of error tips can be easily integrated into the hardware and/or workflow for loading and transferring samples used in the processing module.

The tip waste rack may be transferred from the tip waste rack position to the adjacent sample rack position either at the same time as the sample rack in the adjacent sample rack position is transferred and held in the empty SWAP rack holding mechanism or after transferring the sample rack in the adjacent sample rack position to the SWAP rack holding mechanism. In one embodiment, the SWAP rack holding mechanism may be a transport mechanism which runs simultaneously without interfering with the transport mechanism which transfers the tip waste rack. In another embodiment, the SWAP rack holding mechanism is an additional position for holding sample racks. In this embodiment, the processing module will require at least four positions for holding sample racks to perform the method. An advantage of this embodiment is that only one rack transport mechanism for transporting racks in one direction at a time is required in the processing module. In one specific embodiment, the empty SWAP rack holding mechanism comprises a transport mechanism or a sample rack position.

In one specific embodiment the steps of the present method are repeated until all tip receiving openings of the tip waste rack hold a pipette tip.

In one specific embodiment of the present method, the tip waste rack is automatically removed from the processing module when all tip receiving openings of the tip waste rack hold a pipette tip, and a tip waste rack with empty tip receiving openings is provided to the processing module, or the tip waste rack is automatically removed when a new tip waste rack is loaded. If the tip waste rack is automatically removed when the new tip waste rack is loaded, the tip waste rack which is removed is at least partly full.

In order to load racks into the automated processing module, and unload racks from the processing module, the method described herein comprises a processing module with at least one sample rack loading and unloading workflow, and wherein said waste tip rack is loaded and unloaded via said workflows. A sample rack loading workflow is, thus, a workflow for loading the sample racks into the automated processing module. In one specific embodiment, the loading workflow is also automated. The tip waste racks are, thus, loaded using the loading workflow that is used for loading sample racks. The automated processing module also has to comprise an unloading workflow for sample racks which are no longer required for sample transfer. The module, thus, comprises a workflow for such unloading of sample racks from the module. In one specific embodiment, the unloading workflow is also automated. Thus, when all tip receiving openings of the tip waste rack are occupied by pipette tips, and the tip waste rack has to be removed in order to be replaced by a tip waste rack with empty tip receiving openings, the tip waste rack which has all tip receiving openings occupied by tips is removed from the module by the sample rack unloading workflow. A tip waste rack with empty tip receiving openings is then loaded by the sample rack loading workflow of the processing module. In one specific embodiment, said at least one sample rack loading workflow comprises a priority loading workflow or a regular loading workflow, and said tip waste rack is loaded via said priority loading workflow or said regular loading workflow. In one specific embodiment, said at least one sample rack unloading workflow comprises an error rack unloading workflow, and said waste tip rack is unloaded via said error rack unloading workflow or a regular rack unloading workflow. A regular loading workflow is meant to be the workflow by which sample racks are commonly loaded onto the processing module. The priority loading workflow is a workflow intended to allow sample racks which carry priority samples to be analyzed before samples that were already loaded but do not need to be analyzed with priority. The tip waste rack may, thus, be loaded also via the priority loading workflow.

In one embodiment, said tip waste rack comprises an identifier. The tip waste rack is identified upon loading or unloading by an identification device for reading said identifier comprised in the processing module. In one specific embodiment, said identifier is a barcode or an RFID tag, and said identification device is a barcode reader or a RFID reader.

In one embodiment of the method described herein, the loading and unloading of the tip waste rack is tracked by a computer controller. In a specific embodiment of the method, the identification device for reading said identifier reads the identifier of the loaded waste tip rack and transfers the information on the identity of the tip waste rack to the computer controller.

An embodiment further relates to a processing system comprising a processing module. The processing module comprises at least three positions for holding sample racks. At least one sample rack comprises sample tubes holding a liquid sample located in one of said at least three positions. At least one tip waste rack comprises tip receiving openings located in another of said at least three positions. A SWAP rack holding mechanism is also comprised, as well as at least one processing tube, a pipette head for transferring samples from a sample tube to a processing tube and a transfer mechanism for transferring the tip waste rack from said position holding the tip waste rack to a position adjacent to the position holding the sample rack. Specific embodiments of the system are as described herein. In one embodiment, the processing module is comprised in an automated analyzer.

In one embodiment, the system comprises a computer controller for controlling the method as described herein.

An embodiment also relates to an automated process of transferring samples from a sample tube to a processing tube in a processing module, comprising tracking the loading status of tip receiving openings in a tip waste rack present in said processing module, wherein said loading status is either empty or loaded with a pipette tip. The transferring of sample proceeds if a minimum of empty tip receiving openings is present in the tip waste rack. In one specific embodiment, the minimum of empty tip waste tubes is defined as all tip waste tubes present in one tip waste rack. In another specific embodiment, if the tip waste rack comprises five tip receiving openings, the minimum of empty tip receiving openings present in the tip waste rack would be five in order for the process of transferring samples to proceed.

In one embodiment, the process of transferring samples is only started if a tip waste rack is held in the position for holding a tip waste rack. In a more specific embodiment, the process is only started if the minimum of empty tip waste tubes is present in the tip waste rack comprised in the processing module.

Embodiments of the method and process and system provide the advantage that automated workflows of the processing module can be adapted for tip wasting such that no user interaction is necessary for removing error tips. This provides true walk-away time and no or less maintenance time as no process interruption for un- and reloading is necessary. Further advantages are as described herein.

In one embodiment, the processing module may be a sample transfer module in a larger fully automated analyzer and system. The analyzer may comprise additional modules, such as a module for enriching, isolating and/or purifying the sample, and a module for analyzing the sample. In one embodiment, the analyzer may detect or quantitate an analyte. In one specific embodiment, the analyzer may be a nucleic acid analyzer which separates and detects or quantitates a target nucleic acid potentially present in a sample.

The term "detecting" as used herein relates to a qualitative test aimed at assessing the presence or absence of an analyte in a sample.

The term "quantitating" as used herein relates to the determination of the amount or concentration of an analyte present in a sample.

The term "analyte" as used herein may be any type of biomolecule which is of interest for detection, and the detection thereof is indicative of a diagnostic status of an organism. The organism can be animal or, more preferably, human. Analytes may be polypeptides, antibodies or nucleic acids. In one embodiment, the analyte is a target nucleic acid.

A "target nucleic acid" is a polymeric compound of nucleotides as known to the expert skilled in the art. "Target nucleic acid" is used herein to denote a nucleic acid in a sample which should be analyzed, i.e. the presence, non-presence and/or amount thereof in a sample should be determined. The target nucleic acid may be a genomic sequence, e.g. part of a specific gene, or RNA. In other embodiments, the target nucleic acid may be viral or microbial.

Detecting or quantitating may be performed by amplification. The term "amplification" as used herein generally refers to the production of a plurality of nucleic acid molecules from a target nucleic acid wherein at least one primer hybridizes to specific site on the target nucleic acid molecules in order to provide an initiation site for extension by a polymerase. Amplification can be carried out by any method generally known in the art, such as but not limited to: standard PCR, long PCR, hot start PCR, qPCR, RT-PCR and Isothermal Amplification. Other amplification reactions comprise, among others, the Ligase Chain Reaction, Polymerase Ligase Chain Reaction, Gap-LCR, Repair Chain Reaction, 3SR, NASBA, Strand Displacement Amplification (SDA), Transcription Mediated Amplification (TMA), and Qb-amplification.

In FIG. 1, processing module (2) has multiple positions for holding sample racks (3, 3a,b,c, 11). One of the positions is a tip waste rack holding position (3a) which holds a tip waste rack (5) comprising tip receiving openings (6). The processing module (2) further has a position for holding a sample rack (3b) which holds a sample rack (4a) comprising sample tubes (7) and an adjacent position for holding a sample rack (3c) which may hold a sample rack (4b). For a pipette (1) which is used for transferring samples, an error is detected. In this case, the sample rack (3c) in the adjacent sample rack position (4b) is transferred to the SWAP position (11), which, in this embodiment, is also a position for holding a sample rack, but may be also constituted differently, e.g., as a second transport mechanism. The transfer is affected by transport mechanism (10). Also shown in FIG. 1 is a plate comprising processing tubes (9) into which the samples are transferred from sample tubes (7). The processing cell comprises a loading lane (17) through which sample racks are loaded by loading workflow (14). The processing module further comprises a regular unloading lane (15) and an error lane (13). Error racks are unloaded via lane (13) by error unloading workflow (16) or a regular rack unloading workflow (19). The processing module (2) also comprises a reader (12) for reading an identifier placed on the sample racks (4a, 4B) and tip waste racks (5).

Figure 2A:
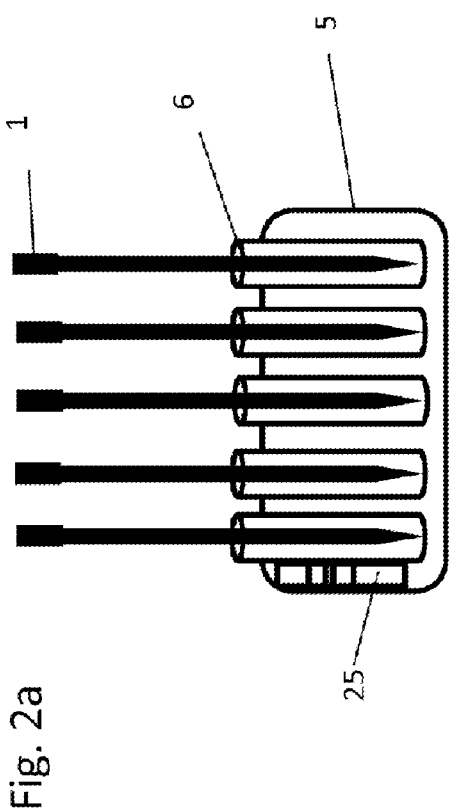
FIG. 2 shows, in a), a tip waste rack with pipette tips; and in b) a sample rack holding sample tubes which comprise liquid samples.

FIG. 2a shows an exemplary embodiment of a tip waste rack (5) which comprises sample tubes (6) as tip receiving openings for tips (1). The tip waste rack (5) has a barcode (25) fixed thereon by which the reader (12) can identify the rack as a tip waste rack (5).

Figure 2B:
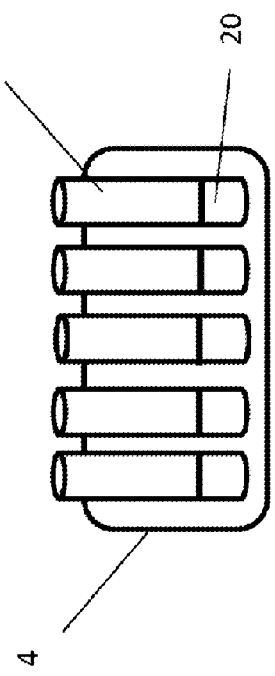

FIG. 2b shows a sample rack (4) with sample tubes (7) which may be identical to sample tubes (6). The sample tubes (7) comprise a liquid sample (20) which may comprise an analyte.

Figure 3:
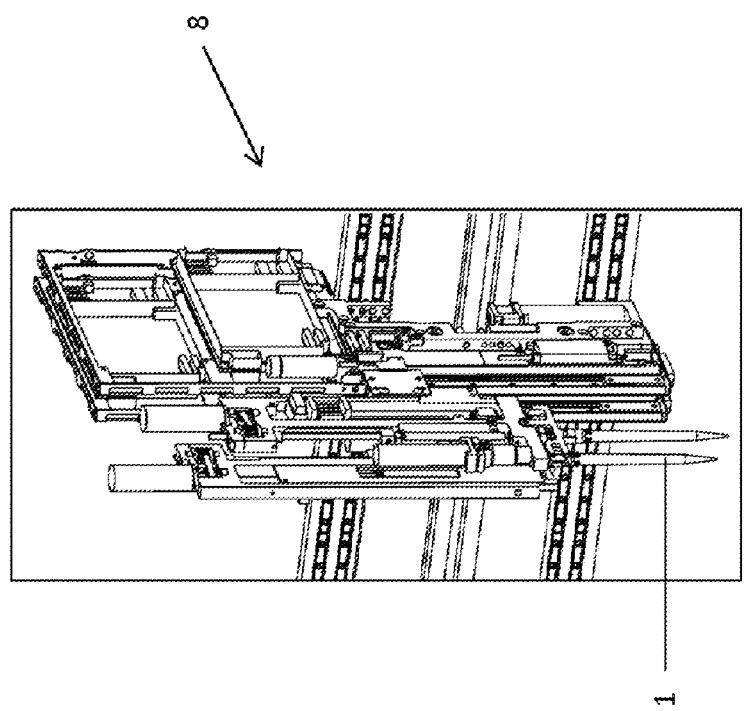
FIG. 3 shows a perspective view of a pipetting device.

In FIG. 3, an exemplary embodiment of a pipette head (8) engaged to pipette tips (1) is shown.

FIG. 4 shows a processing system (40) comprising a computer controller (30) and a processing module (2). The processing system (40) further comprises a module (32) for enriching, isolating and/or purifying an analyte, and a module (31) for reacting and detecting an analyte. The processing system further comprises a loading deck (37) which has a loading lane (33) used by a regular loading workflow (35) for loading sample racks (4) or tip waste racks (5), and connected to workflow (14). The loading deck (37) further comprises an unloading lane (34) used by a regular unloading workflow (36) to unload sample racks (4). Tip waste racks may also be unloaded by workflow (36). Alternatively, tip waste racks are unloaded via the error lane (13) (see FIG. 1) by error unloading workflow (16).

While the foregoing embodiments have been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. An automated method of wasting tips in an automated processing module, said processing module comprising at least three positions for holding racks, wherein one of said positions is a tip waste rack position holding a tip waste rack, wherein said tip waste rack comprises tip receiving openings; at least two of said positions are sample rack positions for holding a first sample rack and a second sample rack, wherein at least said first sample rack comprises sample tubes holding a liquid sample, wherein two of said sample rack positions are adjacent of each other; a pipette head for transferring the samples from the sample tubes to processing tubes using pipette tips; at least one rack transport mechanism, and a rack holding position, the method comprising the sequential steps of:
   a) detecting an error in at least one pipette tip used for transferring the samples from the sample tubes held in the first sample rack to the processing tubes;
   b) transferring the second sample rack from the adjacent sample rack position to an empty rack holding position within the processing module with the rack transport mechanism;
   c) transferring the tip waste rack from the tip waste rack position to the adjacent sample rack position with the rack transport mechanism;
   d) discarding the at least one pipette tip for which an error was detected by ejecting it from the pipette head into one of the tip receiving openings of the tip waste rack;
   e) transferring the tip waste rack to the tip waste rack position with the rack transport mechanism; and
   f) transferring the second sample rack from the rack holding position to the adjacent sample rack position with the rack transport mechanism.

2. The method of claim 1, wherein steps a) to f) are repeated until all tip receiving openings of the tip waste rack hold a pipette tip.

3. The method of claim 1, wherein the tip waste rack is automatically removed from the processing module when all tip receiving openings of the tip waste rack hold a pipette tip, and a tip waste rack with empty tip receiving openings is provided to the processing module, or the tip waste rack is automatically removed when a new tip waste rack is loaded.

4. The method of claim 1, wherein said error detection comprises clot detection, liquid level detection failure, handling failure, mechanical errors, software failure or hardware failure.

5. The method of claim 1, wherein said pipette tip is discarded by selective tip detachment from the pipette head.

6. The method of claim 1, wherein said processing module comprises at least one sample rack loading and unloading workflow wherein the sample racks are loaded through a loading lane, and wherein said tip waste rack is loaded and unloaded via said workflow.

7. The method of claim 1, wherein said tip waste rack comprises an identifier and wherein said tip waste rack is identified upon loading or unloading by an identification device for reading said identifier comprised in the processing module.

8. The method of claim 7, wherein said loading and unloading is tracked by a computer controller.

9. The method of claim 1, wherein said empty rack holding position comprises a second transport mechanism or a sample rack position.

10. The method of claim 1, wherein said pipette head comprises at least two interfaces for engaging with pipette tips.

11. The method of claim 1, wherein the number of tip receiving openings and interfaces for engaging pipette tips are identical.

12. The method of claim 1, wherein the tip waste rack has the same dimensions as the sample rack.

\* \* \* \* \*